United States Patent
Groscurth et al.

(10) Patent No.: US 10,213,275 B2
(45) Date of Patent: Feb. 26, 2019

(54) CUSTOM LINKABLE IMAGING AND MULTIFUNCTIONAL TRAY

(71) Applicants: Randall C. Groscurth, Troy, MI (US); Shoko U. Groscurth, Troy, MI (US)

(72) Inventors: Randall C. Groscurth, Troy, MI (US); Shoko U. Groscurth, Troy, MI (US)

(73) Assignee: IBUR, LLC, Troy, MI (US)

( * ) Notice: Subject to any disclaimer, the term of this patent is extended or adjusted under 35 U.S.C. 154(b) by 0 days.

(21) Appl. No.: 14/981,852

(22) Filed: Dec. 28, 2015

(65) Prior Publication Data

US 2016/0106517 A1    Apr. 21, 2016

Related U.S. Application Data

(63) Continuation of application No. 12/911,168, filed on Oct. 25, 2010, now Pat. No. 9,226,801.

(60) Provisional application No. 61/370,950, filed on Aug. 5, 2010, provisional application No. 61/311,595, filed on Mar. 8, 2010.

(51) Int. Cl.
| | |
|---|---|
| *A61C 9/00* | (2006.01) |
| *A61C 1/08* | (2006.01) |
| *A61B 19/00* | (2006.01) |
| *A61B 5/055* | (2006.01) |
| *A61B 5/00* | (2006.01) |
| *A61B 6/14* | (2006.01) |
| *A61B 6/00* | (2006.01) |

(52) U.S. Cl.
CPC .............. *A61C 1/084* (2013.01); *A61B 19/54* (2013.01); *A61C 9/004* (2013.01); *A61C 9/0046* (2013.01); *A61B 5/055* (2013.01); *A61B 5/4547* (2013.01); *A61B 6/14* (2013.01); *A61B 6/583* (2013.01); *A61B 2019/5466* (2013.01)

(58) Field of Classification Search
CPC ..... A61C 9/0006; A61C 9/004; A61C 9/0046; A61C 1/084; A61B 19/54
See application file for complete search history.

(56) References Cited

U.S. PATENT DOCUMENTS

| | | | |
|---|---|---|---|
| 5,015,183 | A | 5/1991 | Fenick |
| 5,443,386 | A | 8/1995 | Viskup |
| 6,671,539 | B2 | 12/2003 | Gateno et al. |

(Continued)

FOREIGN PATENT DOCUMENTS

| | | |
|---|---|---|
| CA | 2484475 A1 | 4/2006 |
| WO | WO-2002/096261 A2 | 12/2002 |

(Continued)

OTHER PUBLICATIONS

International Search Report for PCT/US2011/027206 (4 pages).
European Examination Report for EP11710927.2, dated May 3, 2016.

*Primary Examiner* — Ralph Lewis
(74) *Attorney, Agent, or Firm* — Fishman Stewart PLLC (57) ABSTRACT

A multifunctional diagnostic tray configured to clasp an oral structure when positioned in a mouth. The tray may be digitally designed from surface scan data of the mouth and manufactured. The tray provides a temporary positioning reference location that may be viewed in a tomography scan data set. The tray may be used to orient and verify the tomography scan data set and the surface scan data set to create a combined master data file that may be used to determine the appropriate location for a dental implant or other dental procedure.

21 Claims, 6 Drawing Sheets

(56) References Cited

U.S. PATENT DOCUMENTS

| | | | |
|---|---|---|---|
| 7,044,735 B2* | 5/2006 | Malin | A61C 1/084 433/215 |
| 7,273,370 B2* | 9/2007 | Kohani | A61C 9/0006 433/37 |
| 9,226,801 B2* | 1/2016 | Groscurth | A61C 1/084 |
| 2002/0051951 A1 | 5/2002 | Chishti et al. | |
| 2006/0240378 A1 | 10/2006 | Weinstein et al. | |
| 2006/0241406 A1 | 10/2006 | Noujeim | |
| 2006/0257817 A1* | 11/2006 | Shelton | A61C 8/0089 433/75 |
| 2008/0025463 A1 | 1/2008 | Lang | |
| 2008/0085489 A1* | 4/2008 | Schmitt | A61C 1/084 433/75 |
| 2008/0166681 A1* | 7/2008 | Weinstein | A61C 1/084 433/76 |
| 2008/0171305 A1 | 7/2008 | Sonenfeld et al. | |
| 2008/0194949 A1 | 8/2008 | Yang et al. | |
| 2008/0253506 A1 | 10/2008 | Zuendorf et al. | |
| 2008/0286715 A1 | 11/2008 | Choi | |
| 2009/0162813 A1 | 6/2009 | Glor et al. | |

FOREIGN PATENT DOCUMENTS

| | | |
|---|---|---|
| WO | WO-2008/117323 A1 | 10/2008 |
| WO | WO-2009/141716 A2 | 11/2009 |

\* cited by examiner

CUSTOM LINKABLE IMAGING AND MULTIFUNCTIONAL TRAY

RELATED APPLICATIONS

This application is a continuation of U.S. patent application Ser. No. 12/911,168 (U.S. Pat. No. 9,226,801), filed on Oct. 25, 2010, which claims priority to U.S. Provisional Application No. 61/311,595, filed Mar. 8, 2010 and U.S. Provisional Application No. 61/370,950, filed Aug. 5, 2010. All of the foregoing applications are hereby incorporated by reference in their entirety.

FIELD

The present disclosure relates to a dental device.

BACKGROUND

When preparing for a dental procedure, including dental implants, bone grafting and maxillofacial reconstruction, accurately determining an ideal location in the mouth for the procedure can be paramount to its success. For example, when inserting a dental implant, the patient's bone structure, the condition of the patient's bone density, and the presence of other oral structures in the mouth may effect where an implant is positioned. Therefore, a dentist and/or dental technician must be aware of the anatomical structures below the gum tissue, as well as, any structures located above the gum tissue.

Tomography scans have been used to capture images of structures located above and below the gum tissue. However, tomography scans including computerized tomography (CT) scan images, cone beam computerized tomography (CB CT) scan images, magnetic resonance imaging (MRI) scan images, and other 3D imaging devise are subject to image scattering when certain materials such as filings or crowns are present in a mouth. Thus, tomography scans may be unreliable, inaccurate and unusable as a proper diagnostic tool.

Surface scans including intra-oral scanners, optical image scanners, and laser image scanners have also been used to capture images of structures located in a mouth. However, surface scans may not accurately depict structures existing below the gum tissue.

Given scatter and other types of inaccuracies in the data, simply aligning an outline of oral structures in tomography scan data to an outline of the same structures in surface scan data may not accurately represent the location of oral structures within a mouth. Therefore, there is a need for a device that may be used to accurately align tomography scan data and surface scan data to provide a more accurate representation of a mouth. There is also a need for a system for using the device to more accurately align the tomography scan data set and the surface scan data.

DETAILED DESCRIPTION

Referring now to the discussion that follows and also to the drawings, illustrative approaches are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

Figure 1:
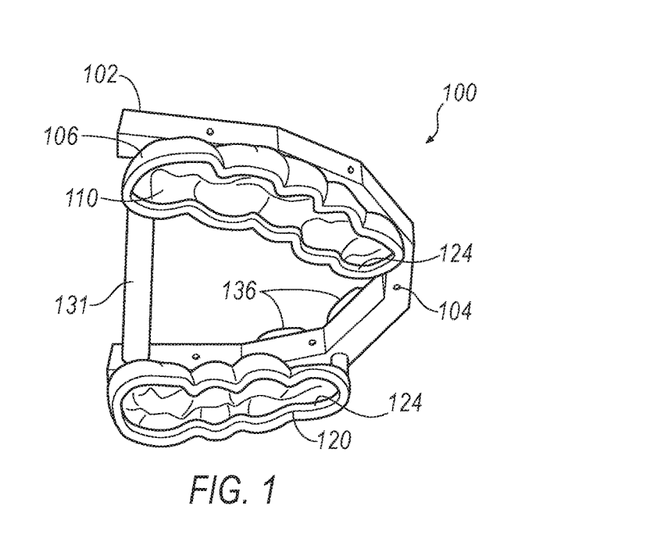
FIG. 1 is an exemplary multifunctional tray

FIG. 1 illustrates an exemplary custom linkable multifunctional tray 100 that allows accurate combining and linking of data from different imagining devices. The multifunctional tray 100 may take many different forms and include multiple and/or alternate components. While an exemplary multifunctional tray 100 is shown in FIG. 1, the exemplary components illustrated in the figure are not intended to be limiting. Indeed, additional or alternative components and/or implementations may be used. An exemplary method of manufacturing the multifunctional tray 100 and a system for using the multifunctional tray 100 to combine and link data are also described in more detail below.

Multifunctional tray 100 may include a frame 102 and at least one marker 104. The tray 100 may also include a clasping portion 106. However, some exemplary trays may be comprised of marker 104 and clasping portion 106.

Clasping portion 106 may have at least one tooth receiving cavity 110 formed therein. However, as illustrated in FIG. 1, clasping portion 106 may also have a plurality of teeth receiving cavities. The teeth receiving cavities 110 may be designed to extend along the entire dental arch of a patient when the tray 100 is inserted into a mouth. The teeth receiving cavities 110 may also be designed to extend partially along the dental arch of a patient when the tray 100 is inserted into a mouth. As illustrated in FIG. 1, when tray 100 is inserted, the teeth receiving cavities 110 are designed to extend partially along opposing sides of a dental arch. However, other exemplary trays may include teeth receiving cavities 110 designed to extend partially along the front of the dental arch when the tray 100 is inserted. The number and location of the teeth receiving cavities 110 may be determined by the oral structures present in a mouth and/or the type of treatment needed. Although described as a tooth receiving cavity, the clasping portion 106 may be designed to contact, clasp, or otherwise engage various oral structures including, but not limited to, implants, prostheses, and gum tissue.

Figure 2A:
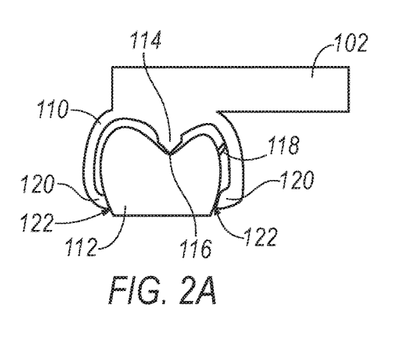
FIG. 2a is an exemplary tooth receiving cavity.
Figure 4:
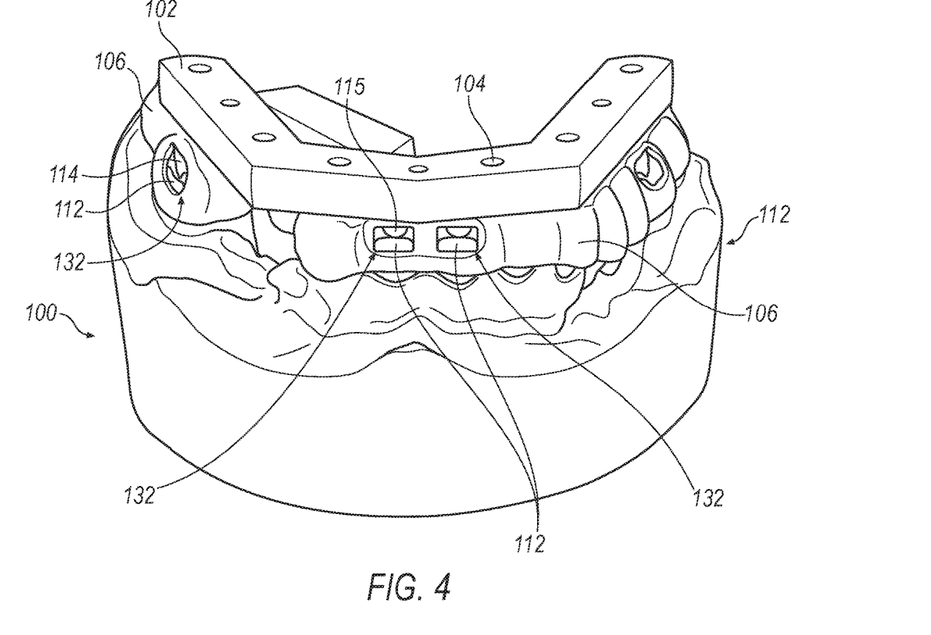
FIG. 4 is an exemplary multifunctional tray having a window.

As illustrated in FIG. 2a, the tooth receiving cavity 110 may be designed to have limited occlusal surface contact with an oral structure 112. That is, the tooth receiving cavity 110 may not engage the entire tooth or other oral structure 112. For example, the tooth receiving cavity 110 may include at least one occlusal rest 114. The occlusal rest 114 may extend inwardly from the tooth receiving cavity 110 and may contact the occlusal surface of the oral structure 112 at an occlusal contact point 116. Although illustrated as substantially triangular in FIG. 2a, occlusal rest 114 may take on a variety of shapes. Indeed, the occlusal rest 114 may be designed and customized to fit the unique oral features of a patient. The occlusal rest 114 may also be formed integrally with the tooth receiving cavity 110, the manufacture of which will be discussed in more detail below. In other exemplary embodiments, the tooth receiving cavity 110 may also be designed to have limited incisal surface contact or limited crest of the ridge surface contact with an oral structure 112. That is, the tooth receiving cavity 110 may include at least one incisal rest 115 or, as illustrated in FIG. 4, the tooth receiving cavity may have a combination of occlusal rests 114 and incisal rests 115.

In addition to providing limited surface contact, the occlusal rest 114 and/or the incisal rest 115 may assist in stabilizing clasping portion 106 when tray 100 is inserted into a mouth. Referring back to FIG. 2a, the tooth receiving cavity 110 may also include one or more stabilizing rests 118. Similar to the occlusal rest 114 and the incisal rest 115, the stabilizing rest 118 may extend inwardly from the tooth receiving cavity 110 and contact an oral structure 112. However, the stabilizing rest 118 may be designed to contact the occlusal surface, the incisal surface, or any other surface of an oral structure 112. The stabilizing rest 118 may also take on a variety of shapes and may be customized to fit the unique oral features of a patient. The stabilizing rest 118 may also be formed integrally with the tooth receiving cavity 110. Although FIG. 2a is illustrated as having one stabilizing rest 118, a plurality of stabilizing rests 118 may be used when designing the clasping portion 106.

The tooth receiving cavity 110 may also be designed to contact, clasp, or otherwise engage the undercut of an oral structure 112. That is, the tooth receiving cavity 110 may include an undercut clasp 120 that allows the tray 100 to remain in position once the tray 100 is inserted into a mouth. The undercut clasp 120 may extend inwardly from the tooth receiving cavity 110 such that the undercut clasp 120 engages a lateral surface of the oral structure 112 at a lateral contact point 122. As illustrated in FIG. 2a, a lateral contact point 122 may be formed between a plurality of undercut clasps 120 and the oral structure 112. However, other configurations may be used.

Figure 2B:
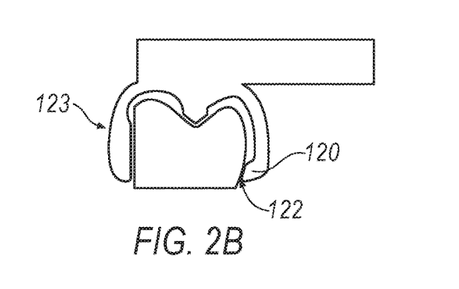
FIG. 2b is an exemplary tooth receiving cavity.

For example, FIG. 2b illustrates lateral contact point 122 as a single contact point between the undercut clasp 120 and the oral structure 112. However, FIG. 2b also illustrates an opposing portion 123 of the tooth receiving cavity 110 in reciprocating contact with the oral structure 112. The reciprocating contact allows the clasping portion 106 to reciprocate back and forth along the surface of the tooth during installation and removal of the tray 100. The reciprocating contact prevents an oral structure 112 from moving during installation and removal.

Figure 3A:
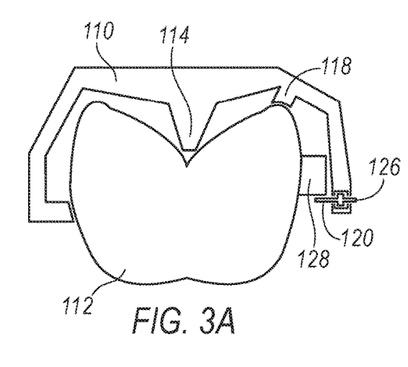
FIG. 3a is an exemplary tooth receiving cavity.
Figure 3B:
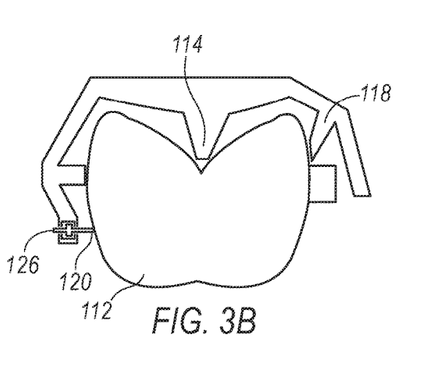
FIG. 3b is an exemplary tooth receiving cavity.

The undercut clasps 120 may be formed using a material flexible enough to allow clasping portion 106 to engage the teeth, gum tissue or other oral structures. The undercut clasps 120 may be formed integrally with the teeth receiving cavities, discussed in more detail below, or they may be formed separately. For example, the undercut clasps 120 may be snap-lock hinges, screws, pegs, or other suitable structures. Such structures may be used when a patient has an orthodontic appliance, such as braces. As illustrated in FIG. 3a, tooth receiving cavity 110 is configured to accept a screw, bolt, or other suitable structure. The screw 126 may be used to engage a surface of an orthodontic appliance 128 to create an undercut clasp 120. However, as illustrated in 3b, the screw 126 or other suitable structure may also be used to engage a surface of an oral structure 112 to create an undercut clasp 120.

The tooth receiving cavity 110 may also include a lateral band 124. The lateral band 124 may also be designed to contact, clasp, or otherwise engage an oral structure 112. Referring back to FIG. 1, the lateral band 124 may extend inwardly from the clasping portion 106 and along the perimeter of the tooth receiving cavities 110. As illustrated, when the tray is installed, the lateral band 124 creates a band of contact between the clasping portion 106 and the oral structure 112. The lateral band 124 may be a continuous band or the lateral band 124 may be formed from multiple sections. The lateral band 124 may also be formed around a plurality of teeth or the undercut band 124 may be formed around a single tooth, an implant, a prosthesis, gum tissue, or any other suitable oral structures capable of supporting the tray 100.

Although illustrated in FIG. 1 as engaging the undercut of each oral structure in contact with the clasping portion 106, the lateral band 124 may be designed to meet the needs of a particular mouth. For example, portions of the lateral band 124 may engage the undercut of an oral structure 112 and some portions of the band may contact a lateral surface of the oral structure 112 in order to assist in stabilizing the tray 100 or to provide reciprocating contact with the oral structure 112. Portions of the lateral band 124 may also be used to define a space between an oral structure 112 and a certain area or areas of the tooth receiving cavity 110 and portions of the band may not contact an oral structure at all. Accordingly, the lateral band 124 may be designed on different planes of the clasping portion 106 instead of just in one plane as illustrated in FIG. 1. That is, a portion of the lateral band 124 may engage the undercut of one oral structure and contact an upper lateral surface of an adjacent oral structure to define a space between the oral structure 112 and the tooth receiving cavity 110. Therefore, the lateral band 124 may be designed and customized to fit the unique oral features of a patient. The lateral band 124 may also be formed integrally with the tooth receiving cavity 110, the manufacture of which will be discussed in more detail below.

The lateral band 124 may assist in stabilizing the clasping portion 106 by contacting the sub equatorial areas of an oral structure or a plurality of oral structures when tray 100 is inserted into a mouth. The lateral band 124 may also maintain the tray 100 in position once the tray 100 is inserted into a mouth.

The use of the occlusal rest 114, the incisal rest 115, the undercut clasp 120, and/or the lateral band 124 allows the tray 100 to be placed tightly and securely onto a single tooth, multiple teeth and/or other oral structure. This eliminates the concern that the device may dislocate while being worn by the patient. This design also allows the device to fit securely onto an oral structure or structures with near perfect repeatability. The clasping portion 106 may also be designed to be placed tightly and securely onto gum tissue for use in edentulous or partially edentulous patients.

The clasping portion 106 may also have one or more windows 132 formed in the teeth receiving cavities 110 to determine whether the tray 100 is positioned correctly in a mouth. As illustrated in FIG. 4, the window 132 may be formed in areas of the teeth receiving cavities 110 where an occlusal rest 114 and/or an incisal rest 115 is positioned. The window 132 allows a doctor and/or a technician to verify that the tray 100 is positioned accurately in the mouth by observing the position of the occlusal rest 114 and/or in the incisal rest 115 with respect to the occlusal surface or the incisal surface of a tooth or other oral structures. Although window 132 is illustrated as rectangular in shape, the window 132 may be formed as any suitable shape that allows a doctor and/or technician to view the position of the occlusal rest 114 and/or the incisal rest 115.

Referring back to FIG. 1, the frame 102 may be positioned adjacent to a top outer surface of the clasping portion 106. As illustrated in FIG. 1, the frame 102 may extend along a top outer surface of the clasping portion 106 opposite the teeth receiving cavities 110. The frame 102 may extend along the entire top outer surface of the clasping portion 106 or the frame 102 may extend along a portion of the clasping portion 106. The frame 102 may include a stabilizing bar 131. In some cases, the frame 102 may have a stop 136. The stop 136 may be used to prevent oral structure(s) of the opposing dental arch from contacting the tray 100 when the tray 100 is inserted in a mouth.

Figure 5:
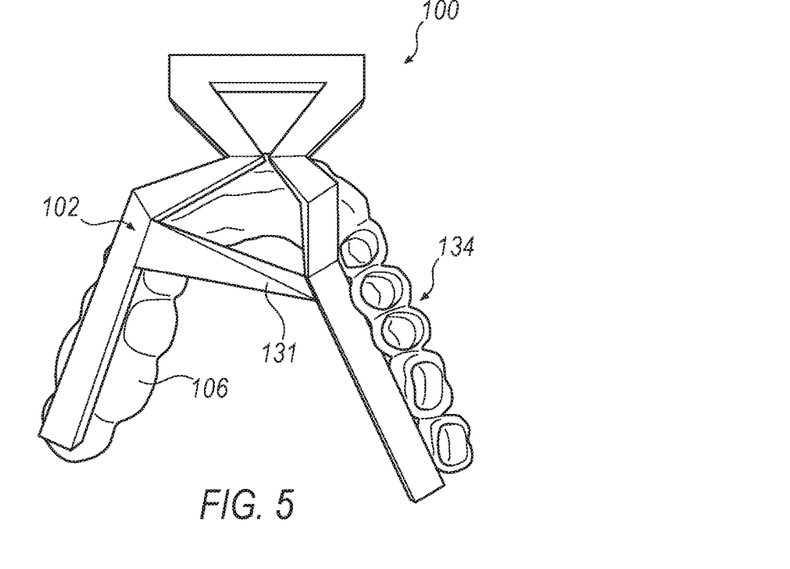
FIG. 5 is a top view of an exemplary multifunctional tray.

In another exemplary tray illustrated in FIG. 5, a first portion of the frame 102 may extend along the top outer surface of the clasping portion 106 and a second portion may extend along an outer lateral surface of the clasping portion 106. The frame 102 may also include a portion that extends outwardly from the dental arch. The portion of the frame 102 extending outwardly from the dental arch may not contact a surface of the clasping portion 106. This portion of the frame 102 may take on any suitable configuration and may be used to ease insertion and removal of the tray 100. The portion of the frame 102 extending outwardly from the dental arch may also be used to determine the position of the frame 102 in a tomography scan.

The frame 102 may be formed integrally with the clasping portion 106 or the frame 102 and the clasping portion 106 may be formed separately and assembled prior to taking a tomography scan of the tray. Although illustrated in FIGS. 1 and 5 as positioned adjacent to the clasping portion 106, the frame 102 may also be partially embedded in the clasping portion 106.

Figure 6:
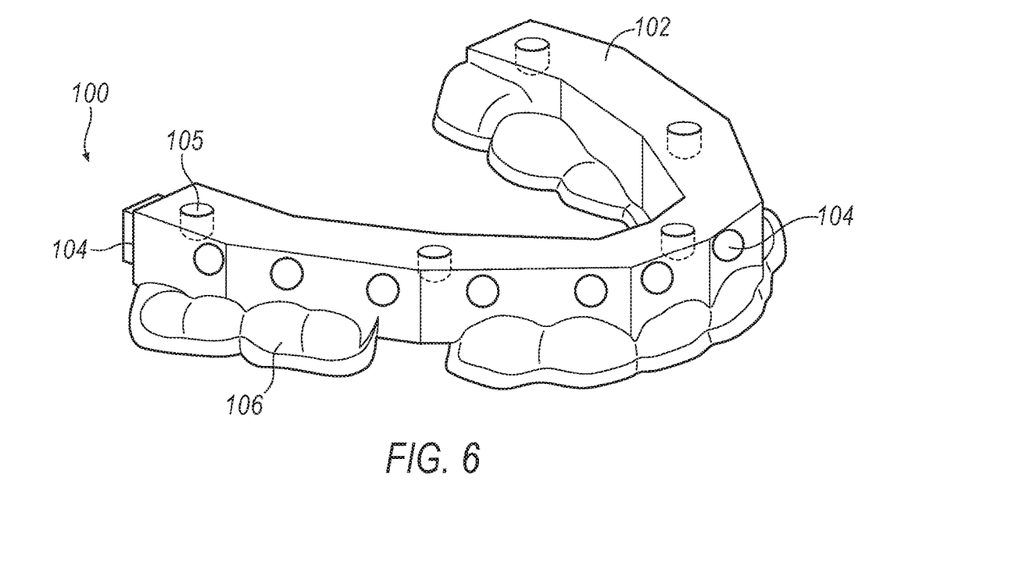
FIG. 6 is an exemplary multifunctional tray having a plurality of markers.

As discussed above, the multifunctional tray 100 may also include at least one marker. The frame 102 may be used to support the marker 104. As illustrated in FIG. 6, the marker 104 or plurality of markers may be disposed substantially within the frame 102, partially disposed within the frame 102, and/or disposed adjacent to the frame 102, or any combination thereof. The marker 104 may be formed integrally with the frame or the marker 104 may be releasably engagable with the frame 102. For example, the frame 102 may include a marker receptor 105 configured to receive a marker 104 or configured to be injected with a radio-opaque material to form a marker 104.

Moreover, in another exemplary tray 100, the marker 104 may be supported by or disposed in the clasping portion 106. The marker 104 may be formed integrally with the clasping portion 106 or the marker 104 may be releasably engagable with the clasping portion 106. For example, the clasping portion may include a marker receptor configured to receive a marker or configured to be injected with a radio-opaque material to form a marker.

Although illustrated as substantially spherical, the marker 104 may be designed as any suitable geometric shape or combination of geometric shapes. For example, the marker 104 may be substantially cuboidal or substantially cylindrical.

The marker 104 may be formed from a radio-opaque material, a non radio-opaque material, or a combination thereof. The radio-opaque material may be a thermoplastic, a ceramic, or any other suitable material, or any suitable combination of materials capable of inhibiting electromagnetic radiation. This allows the marker 104 to be viewable during CT scans, CB CT scans, CB VT scans, MRI scans, and other types of three-dimensional surface scanning. The marker may also be viewable in surface scans.

The marker 104 may also be a radiodensity comparative reference marker. Radiodensity comparative reference markers may be formed using various chemical compositions. This allows the marker 104 to have a different radiodensity based on the chemical composition that is selected. One benefit of using radiodensity comparative reference markers is that the accuracy of the tomography scan data may be evaluated using such markers. For example, CTs or MRIs create a series of two dimensional pictures that may vary in accuracy depending on whether or not the machine is properly calibrated. When reconstructing tomography scan data into three dimensional images, often done with volumization software, a threshold value of grey scale radiodensity may be quantified using a Hounsfield Unit (HU). However, the software threshold value may not be consistent with the threshold value indicated in the scan data file, since each read out of the scan data may be affected by one or more factors such as the calibration of the scanner, the method of image acquisition, the computer software being used, or image scatter. However, the use of a radiodensity comparative reference marker may provide a "built-in" standard. That is, the operator may use a radiodensity comparative reference marker with a known density as a reference to tune the threshold setting of the software for volumization of the data file. This standard may give users a tool to evaluate the tomography data file and to create more accurate bone models.

Another benefit of using radiodensity comparative reference markers is that the reference marker may be used to mimic various degrees of bone density during a tomography scan. Therefore, a radiodensity comparative reference marker with a known density may be used as a reference to tune the threshold settings of the volumization software. This may provide a model with a more accurate representation of a patient's bone density. The condition of patent's bone density can affect the success of a dental treatment, especially with respect to the placement of a dental implant.

Another exemplary marker 104 that may be used with the multifunctional tray 100 is a negative reference marker. By designing a cavity or other similar structure of a certain size and geometric shape into the frame 102 or adjacent to clasping portion 106, a negative linkable marker can be created. This cavity, which is substantially devoid of material, will appear as a geometric shaped black space in the tomography scan data of a patient when the threshold density is set at the same radiodensity density level as the frame 102. This density level may be the same as the density level of skin. The use of a negative reference marker may increase the accuracy of the tomography scan data because the empty space will offer the clearest image of the marker outline without distortion.

As another example, the space defined between the clasping portion 106 and the oral structure 112 may be used as a negative reference marker. The use of the occlusal rest 114, the incisal rest 115 and/or the undercut clasp 120 may create a space between the clasping portion 106 and the oral structure 112. As discussed above, the image of this geometric black space may be used to verify the accuracy of the tomography scan data. The image may also be used to determine whether the tray is positioned correctly in a mouth during the tomography scan.

Although FIG. 6 illustrates a tray 100 having a plurality of markers 104, a single fiducial reference marker may be used to accurately combine and link data from different imagining devices. As discussed above, the single marker may be disposed substantially within the frame 102, partially disposed within the frame 102, and/or disposed adjacent to the frame 102.

Figure 7:
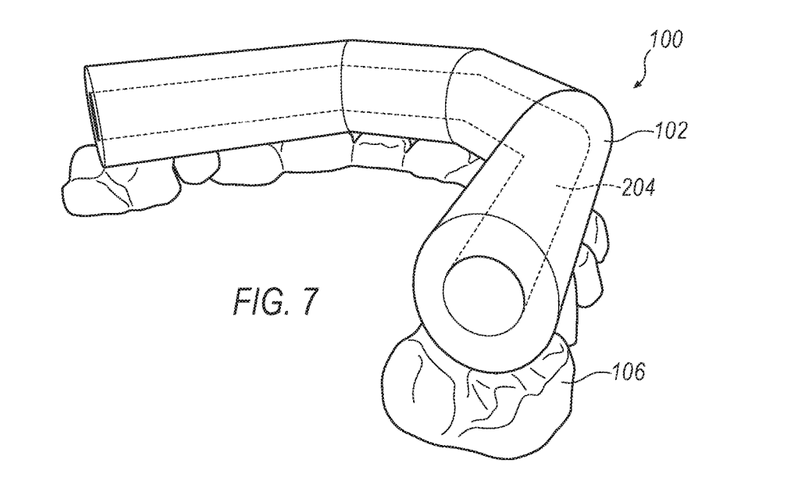
FIG. 7 is an exemplary multifunctional tray having a single fiducial reference marker.

In one exemplary tray 100, as illustrated in FIG. 7, the tray 100 has a clasping portion 106, a frame 102 and single fiducial reference marker 204. In FIG. 7, the frame 102 defines the single fiducial reference marker 204. As illustrated, the single fiducial reference marker 204 may extend along the entire dental arch of a patient. However, the single fiducial reference marker 204 may also be designed to extend partially along the dental arch.

As discussed above, the single fiducial reference marker 204 defined by the frame 102 may be formed from a radio-opaque material, a non radio-opaque material, or a combination thereof. The fiducial reference marker 204 may also be a negative reference marker. Thus, the marker 204 may be viewable in a tomography scan and may be used to combine and link data from different imaging devices, discussed in more detail below. Although not illustrated, the tray 100 in FIG. 7 may also include at least one radiodensity comparative reference marker with a known density that may be used as a reference to tune the threshold settings of the volumization software.

The exemplary multifunctional trays discussed above may be designed using various methods. For example, the multifunctional tray 100 may be designed using a digital dental model of a mouth. The digital dental model may be obtained using a surface scanning device, such as an intra oral scanner, to scan the oral structures present in the mouth. The surface scan data may then be save as a CAD compatible file and opened using a modeling system or other suitable system for appropriate analysis and manipulation. Such systems may include hardware, software or a combination of hardware and software. Surface scan data may also be obtained from surface scanning a dental model of the mouth.

Once the digital dental model has been created from the surface scan data, the frame 102 and the clasping portion 106 may be digitally designed. The clasping portion 106 may be digitally designed on the digital dental model using the hardware and/or software system discussed above. Using the digital dental model, the clasping portion 106 may be designed to fit the unique contours of a mouth, including the contours of individual oral structures. For example, referring back to FIG. 2a, the occlusal rest 114 extending inwardly from tooth receiving cavity 110 may be designed to fit the contours of the occlusal surface of a particular tooth. Similarly, the undercut clasp 120 extending inwardly from a tooth receiving cavity 110 may be designed to fit the contours of the undercut of a particular tooth. Thus, the digital dental model allows a dentist and/or a dental technician to customize a digital tray for each patient based on the oral structures present and/or type of treatment needed.

The frame 102 may also be digitally designed on the digital model using the hardware and/or software system discussed above. The frame 102 may be digitally designed as a single fiducial reference marker 204, as illustrated in FIG. 7 and discussed above. The frame 102 may also be digitally designed to include a single fiducial reference marker and/or plurality of markers 104.

Figure 9:
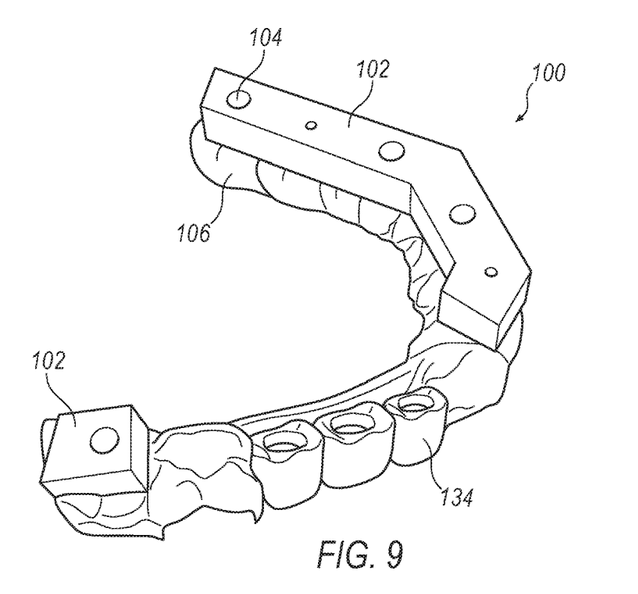
FIG. 9 is an exemplary multifunctional tray having an attachable diagnostic design.

Optionally, as illustrated in FIG. 9, diagnostic teeth 134 and/or components necessary to convert the tray into a diagnostic appliance may be digitally designed. The diagnostic teeth 134 and/or other components may be designed integrally with the digital tray. However the diagnostic teeth 134 and/or the other components may also be designed as separate structures configured to be attachable and detachable to the tray.

Once the components of the digital tray have been designed on the digital model, the tray 100 may be manufactured. The tray may be manufactured using a 3D printer, a stereolithography device, a CNC machine or any other suitable CAM device. The tray 100 may be manufactured from any suitable FDA approved material including, but not limited to, photopolymer, resin, or other radio-transparent/radio-translucent materials. Radio-translucent metals such as Titanium may also be used or added to the tray. If desired, portions of the tray 100 may also be formed by hand. For example, marker 104 may be pre-made and placed into the receptor cites 105 after the tray has been manufactured.

The digital tray design may be saved in a data file with the digital dental model. Thus, the data file includes information related to the position and orientation of the digital tray in relation to the oral structures of a mouth, and may be used as a reference. Use of the data file as a reference is discussed in more detail below.

Figure 8A:
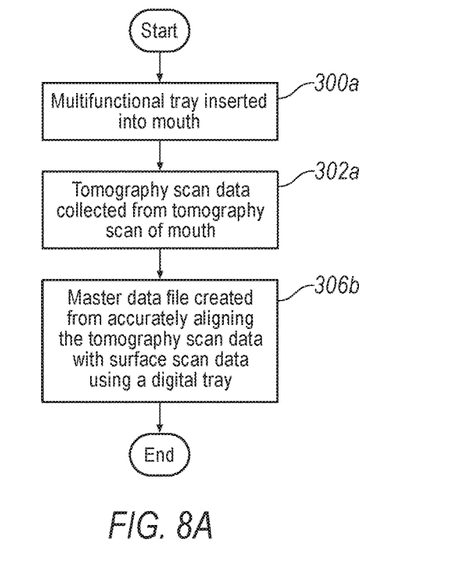
FIG. 8a is an exemplary system of using a multifunctional tray of the type illustrated in FIGS. 1 and 4-7.

FIG. 8a illustrates an exemplary approach for using the tray 100 and the associated digital tray, discussed above, to select a surgical site or to perform other dental procedures, including determining locations for dental implants. As shown in block 300a, the tray 100 may be positioned in a mouth. Once positioned, a doctor may verify that the fit of the tray based on the position of the tray in the mouth and/or by observing the position of an occlusal rest 114 and/or an incisal rest 115 through a window 132, if the tray is configured with such components.

As shown in block 302a, after the tray 100 is positioned, a tomography scan of the mouth may be performed. The tomography scan may be performed using a CT, a CB CT, a CB VT, an MRI, or any other suitable imaging device. Multiple tomography devices may also be used to create different types of tomography images. The data collected from the tomography scan or scans, including the orientation and positioning of the tray, may be used to create a tomography scan data set. In some instances, a surface scan of the mouth may also be performed to create a surface scan data set.

After the tomography scan has been performed, the tomography scan data set and the surface scan data set used to create the digital tray may be aligned to create a combined master data file, as shown in block 304a. To create the combined master data file the tomography scan data may first be analyzed using tomography data volumalizing and converting software. The volumalizing software is used to reconstruct two dimensional pictures into three dimensional images. Using the software, the placement of the tray 100 in a mouth may be verified. That is, the tomography scan data set may be used to measure the position of the tray 100 relative to an oral structure. This measurement may then be compared to the same measurement done using the surface scan data set used to digitally create the tray. Once the tomography scan data has been volumalized and its accuracy verified, the data may be converted to CAD (computer aided design) compatible data and exported to a modeling system or any other suitable system for appropriate analysis and manipulation.

In some situations it may be beneficial to segment different portions of the tomography scan data to create digital models that represent individual sections of a mouth. Indeed, the tomography scan data set may be segmented into portions representing the jaw bone, teeth, roots, nerves, etc. If the tray 100 has at least one radiodensity reference marker, as discussed above, the reference marker may be used to create models of individual sections of an oral structure. That is, different oral structures may have different densities. Thus, by using the reference marker to tune the threshold setting of the software, different oral structure may be viewable in better detail.

Once the tomography scan data has been collected and saved, the surface scan data set including the surface scan data of the mouth and the digital tray, may be opened using the same modeling software. In one exemplary approach, the tomography scan data set may be aligned with or superimposed over the surface scan data set using the digital tray design. As discussed above, the tomography scan data set may be aligned with the surface scan data set using the digital tray having a single fiducial reference marker 204, a single marker or a plurality of markers 104 as a position reference. Use of the digital tray design also allows for additional design options for the dental tray and the marker. For example, the tray 100 may be designed with a marker entirely or partially enclosed in the frame 102 and/or the clasping portion 106. Although an entirely or partially enclosed marker may not be fully detectable in a tomography scan data set and/or a surface scan data set, the marker would be visible when the data sets were aligned using the digital tray design.

When aligning the data sets to create a master data file, the tomography scan data set and the surface scan data set do not have to have a common plane. Instead, each image can be oriented according to the digital design of the device. By aligning the tomography scan data set and the surface scan data set, portions of the tomography scan data distorted by scatter or other inaccuracies may be replaced with more accurate surface scan data.

Although one exemplary approach for aligning the scan data sets is provided, other approaches for aligning the data may be used. For example, multiple data sets may be aligned to create the master data file. Multiple data sets may exist if manual adjustment of the tray 100 was needed to readjust the fit of the tray inside a mouth. In such cases, a doctor or technician may need to surface scan the adjusted tray while the tray is inserted in the mouth or positioned on a dental model. Accordingly, the additional set of surface scan data may need to be aligned to the original surface scan data set and the tomography scan data set in order to create the combined master file. Multiple data sets may also exist if a plurality of tomography scan devices were used to capture the oral structures of a mouth.

The digital tray design may also be used to verify the scaling and sizing of the data contained within the tomography scan data. Verifying the scaling and sizing of the data is important when precision treatment is necessary, such as during implant placement and other oral treatments.

In another exemplary approach, the scan data sets may also be aligned without the digital tray if the tray is designed so that the marker is viewable in the surface scan data. For example, as illustrated in blocks 300b and 302b of FIG. 8b, a tomography scan of the mouth, including the inserted tray 100, may be performed. The tomography scan may be performed using a CT, a CB CT, a CB VT, an MRI, or any other suitable imaging device.

Figure 8B:
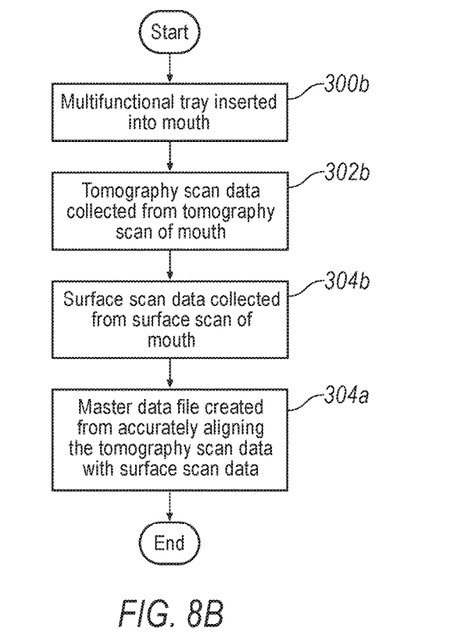
FIG. 8b is an exemplary system of using a multifunctional tray of the type illustrated in FIGS. 1 and 4-7.

A surface scan of the mouth including the tray 100 may also be performed in order to create a surface scan data set, as illustrated in block 304b. The surface scan data may be collected by performing an intra-oral surface scan of the mouth. The surface scan data may also be collected by performing an optical image scan, a laser image scan or any other type of surface scan of a dental model that is created from a dental impression of a mouth, which includes the orientation and positioning of the tray as well as any other oral structures present on the outer surface of the gum tissue and inside the mouth.

After the tomography scan and surface scan have been performed, the tomography scan data set and the surface scan data set may be aligned to create a combined master data file, as illustrated in block 306b. As discussed in more detail above, to create the combined master data file the tomography scan data may first be analyzed using tomography data volumalizing and converting software. Once the tomography scan data has been volumalized and its accuracy verified, the data may be converted to CAD compatible data and exported to a modeling system or any other suitable system for appropriate analysis and manipulation. Such system may include hardware, software or a combination of software and hardware.

When the tomography scan data set has been translated into a file format that corresponds with the surface scan data set, the tomography scan data and the surface scan data may be linked to create a master data file. That is, the presence of the tray 100 including at least one marker in the tomography scan data set and a corresponding tray and marker in the surface scan data set provides a temporary positioning reference location in each data set. These corresponding temporary positioning reference locations enable accurate linking of the data sets because the reference locations present in both scan data sets can be aligned. Thus, the master data file will contain an accurate representation of an entire mouth—the tomography scan data provides imaging of the structures underneath the gum tissue including bone density information and the surface scan data provides imaging of the surface structures of a mouth including oral structures. Moreover, portions of the tomography scan data distorted by scatter or other inaccuracies may be replaced with more accurate surface scan data. Thus, the master data file may be used for evaluation of potential locations for dental procedures or to create a digital or physical diagnostic model.

The linked data from the tomography scan and the surface scan may also be used to verify the scaling and sizing of the data contained within the tomography scan data set and the surface scan data set. Verifying the scaling and sizing of the data is important when precise implant placement is paramount due to the type of implant needed. One way to verify the scaling and sizing of the scanning images is to compare the known size and shape measurements of the tray 100 to the size and shape measurements of digital tray as it appears in the scanning images.

After the data sets have been aligned to create a combined master data file, using the digital design of the tray and/or a marker, the master data file can then be used for evaluation or to create a digital or physical diagnostic model that contains accurate bone structure and tissue representations. Diagnostic designs including teeth, veneers, tissue and implant components may also be added to the master data file.

As illustrated in FIG. 9, the tray 100 may be designed to include attachable and detachable diagnostic teeth 134 or diagnostic teeth that are formed integrally with the tray. The diagnostic teeth 134 may be formed of a radio opaque or non-radio opaque material or a combination thereof. The diagnostic teeth 134 may also be designed as solid or hollow structures, or the diagnostic teeth may be designed to have a veneered surface of a part of a tooth structure. The teeth 134 may be attached to the tray 100 using any suitable method including snapping, sliding, and/or screwing the diagnostic teeth onto the tray in order to determine the aesthetics and the functions of potential implant locations. The diagnostic teeth 134 may also be attached to the tray during tomography scanning so that the teeth are visible in the scan data. The diagnostic teeth 134 may also be designed to be detachable from the tray and attachable to a physical diagnostic model created from the master data file.

Figure 10:
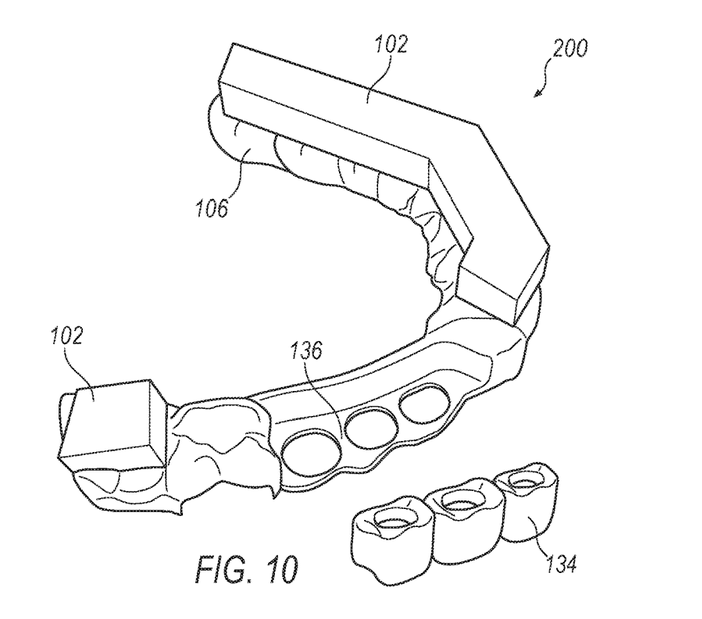
FIG. 10 is an exemplary multifunctional tray.

In another exemplary embodiment, illustrated in FIG. 10, the tray 200 may include a clasping portion 106 and a frame 102. The tray 200 may be designed and configured to be used as the frame for a surgical drill guide, a transfer jig, or other dental appliance. Similar to FIG. 9, the tray 200 may be designed to include integrated, or wholly or partially attachable and detachable diagnostic structures 134. The diagnostic structures may be, but are not limited to, mouth to model or model to model transfer components and diagnostic teeth. The diagnostic structures 134 may be attached to the tray 200 using any suitable method including snapping, sliding, and/or screwing the diagnostic structure onto the tray in order to determine the aesthetics and function of potential implant locations. The diagnostic structure may also be adhered to the tray 100 using a light curable composite or any other suitable adhesive material. The diagnostic structures 134 may also include apertures formed therein such that the tray 200 may be used as a surgical guide, for dental implants and other oral procedures. That is, the tray 200 may be used during a dental procedure to guide a dentist when making an incision, drilling a pilot whole, or inserting an implant.

When the detachable diagnostic structure 134 is removed from the tray 200, the frame may include a tissue contour veneer 136, as illustrated in FIG. 10. The tissue contour veneer 136 represents the top surface of a patient's gum tissue, including the unique contours of the tissue. Thus, the tissue contour veneer 136 may be used to determine where the bottom of an implant may be positioned to provide proper and aesthetically pleasing contouring between the gum tissue and the implant.

Figure 11:
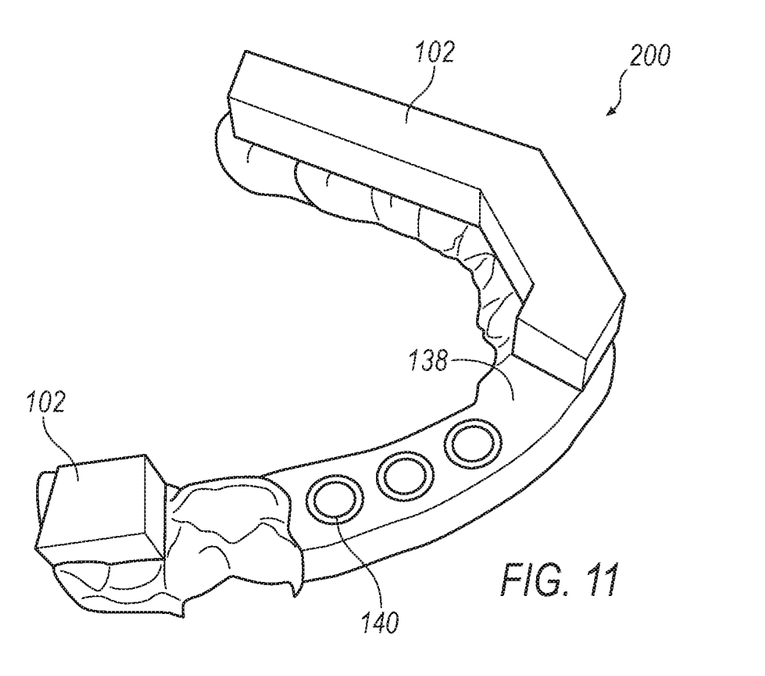
FIG. 11 is an exemplary multifunctional tray.

In another exemplary embodiment, illustrated in FIG. 11, the tray 200 may include a clasping portion 106, a frame 102, and an extension member 138. The extension member 138 may extend between individual sections of clasping portion 106 or the extension member 138 may be designed as part of clasping portion 106. The extension member 138 may include one or a plurality of bushings 140 extending there through. Although, illustrated as tubular bushings, the bushings 140 may take on any suitable shape or structure, including open-face bushings. The bushings 140 may be formed integrally with the extension member 138 or they may be attached to the extension member in any suitable manner. For example, the bushings 140 may be attached to the extension member 138 using a light cured composite material. The bushings 140 may be used to attach diagnostic structures to the tray 200 or to configure the tray 200 into a surgical guide, and implant placement guide, and/or a transfer jig.

The clasping portion 106 of the tray 200 provides an advantage to a dentist when the tray 200 is being used as a surgical guide or transfer jig. That is, the clasping portion 106 allows the tray to be positioned securely to the contours of a mouth. This allows the tray to be inserted, removed and reinserted into the mouth in the same position repeatedly. Thus, when using the tray as a surgical guide, the dentist may rely on the tray to indicate the precise location of an implant site. Moreover, the clasping portion eliminates the need for the tray to be held in place by a dentist, a dental assistant, or a technician during use.

The trays 200 illustrated in FIGS. 10 and 11 may be formed by digitally or manually altering an imaging tray or the trays 200 may be designed and manufactured independently. The clasping portion 106 of the tray 100 may also be utilized in other types of dental appliances including, but not limited to, bite guards, bite splints, night guards, anti-snoring appliance, face bow transfer jigs, bleaching trays, impression trays, orthodontic retainers, orthodontic appliances for bracket placement, orthognathic stents, loose teeth stabilizing appliances, and sleep apnea appliances.

Although the method steps are listed in an exemplary order, the steps may be performed in differing orders. Furthermore, one or more steps may be eliminated and other exemplary steps may be added between the initial stage and the final stage.

The present disclosure has been particularly shown and described with reference to the foregoing illustrations, which are merely illustrative of the best modes for carrying out the disclosure. It should be understood by those skilled in the art that various alternatives to the illustrations of the disclosure described herein may be employed in practicing the disclosure without departing from the spirit and scope of the disclosure as defined in the following claims. It is intended that the following claims define the scope of the disclosure and that the method and apparatus within the scope of these claims and their equivalents be covered thereby. This description of the disclosure should be understood to include all novel and non-obvious combinations of elements described herein, and claims may be presented in this or a later application to any novel and non-obvious combination of elements. Moreover, the foregoing illustrations are illustrative, and no single feature or element is essential to all possible combinations that may be claimed in this or later applications.

All terms used in the claims are intended to be given their broadest reasonable constructions and their ordinary meanings as understood by those knowledgeable in the technologies described herein unless and explicit indication to the contrary is made herein. In particular, use of the singular articles such as "a," "the," "said," etc. should not be read to recite one or more of the indicated elements unless a claim recites an explicit limitation to the contrary.

What is claimed is:
1. A dental tray comprising:
a clasping portion defining a receiving cavity configured to receive at least one oral structure having two opposing outer lateral surfaces and an upper surface disposed therebetween, the clasping portion comprising:
opposing lateral bands unitary with the clasping portion;
a top portion defined therebetween;
at least one rest unitary with the clasping portion and permanently extending away from the top portion into the receiving cavity, the rest shaped and configured to assist in stabilizing the tray;
a lateral contact unitary with the clasping portion and extending away from each of the lateral bands into the receiving cavity;

the receiving cavity defining an open space between both the upper surface and the outer surfaces of the received at least one oral structure;

wherein the top portion is configured to be spaced away from the upper surface of the oral structure with the at least one rest configured to selectively engage the upper surface to facilitate a tight and secure engagement between the clasping portion and the received at least one oral structure;

wherein the lateral contacts selectively engage at least one of the outer surfaces of the received at least one oral structure to facilitate a tight and secure engagement between the clasping portion and the received at least one oral structure; and wherein the orientation of the at least one rest and the lateral contacts ensures that a majority of the received oral structure positioned within the receiving cavity of the dental tray is free from engagement with any element of the dental tray.

2. The dental tray of claim 1, wherein a plurality of the lateral contacts each comprises an undercut clasp configured to extend inwardly into the receiving cavity and to engage the received at least one oral structure, and wherein the undercut clasp has a limited lateral surface contact with the received at least one oral structure.

3. The dental tray of claim 2, wherein the undercut clasp is permanent and more flexible than the at least one rest, and engages the received at least one oral structure by selectively clasping.

4. The clasping portion of claim 2, wherein the undercut clasp is formed separately from the rest of the clasping portion.

5. The dental tray of claim 4, wherein the undercut clasp is at least one of snap-lock hinges, screws, and pegs.

6. The dental tray of claim 1, wherein the at least one rest is one of an occlusal rest and an incisal rest and the at least one oral structure comprises at least one tooth and wherein the one of the occlusal rest and the incisal rest is shaped to fit the contours of a corresponding surface of the at least one tooth when the clasping portion successfully engages the received at least one oral structure.

7. The dental tray of claim 1, further comprising a frame positioned above the clasping portion with the top portion of the clasping portion engaging the frame.

8. The dental tray of claim 7, further comprising a marker configured to be a positioning reference, wherein the marker is supported by at least one of the frame and the clasping portion.

9. The dental tray of claim 8, further comprising a surgical guide supported by at least one extension member connected to at least one clasping portion.

10. The dental tray of claim 1, wherein the receiving cavity defines at least a portion of a negative marker configured to be used for verification of positioning of the at least one oral structure.

11. The dental tray of claim 1, wherein the clasping portion includes at least one window.

12. The dental tray of claim 1, wherein the dental tray is configured to be one of a surgical guide, imaging appliance, sleep appliance and a bite splint.

13. The dental tray of claim 1, wherein at least one distal band is disposed between the two opposing lateral bands.

14. The dental tray of claim 13, wherein the receiving cavity of the clasping portion is enclosed by opposing distal bands, the opposing lateral bands and the top portion.

15. The dental tray of claim 13, wherein at least one distal contact is configured to extend away from the distal band into the receiving cavity, engaging the received oral structure.

16. The dental tray of claim 1, wherein the top portion is a top wall and wherein the lateral bands are lateral walls.

17. A dental tray comprising:
a clasping portion defining a receiving cavity configured to receive at least one oral structure having two opposing outer lateral surfaces and an upper surface disposed therebetween, the clasping portion comprising:
opposing lateral bands unitary with the clasping portion;
a top portion defined therebetween;
at least one rest unitary with the clasping portion and extending away from the top portion into the receiving cavity, the rest shaped and configured to assist in stabilizing the tray;
a lateral contact unitary with the clasping portion and extending away from each of the lateral bands into the receiving cavity and being more flexible than the at least one rest, and configured to engage the received at least one oral structure by selectively clasping;
the receiving cavity defining an open space between both the upper surface and the outer surfaces of the received at least one oral structure;
wherein the top portion is configured to be spaced away from the upper surface of the at least one oral structure with the at least one rest configured to selectively engage the upper surface to facilitate a tight and secure engagement between the clasping portion and the received at least one oral structure;
wherein only the lateral contacts selectively engage the outer surfaces of the received at least one oral structure to facilitate a tight and secure engagement between the clasping portion and the received at least one oral structure; and
wherein the orientation of the at least one rest and the lateral contacts ensures that a majority of the received oral structure positioned within the receiving cavity of the dental tray is free from engagement with any element of the dental tray;
a frame positioned above the clasping portion with the top portion of the clasping portion adjacent the frame; and
a marker configured to be a positioning reference, wherein the marker is supported by at least one of the frame and the clasping portion.

18. The dental tray of claim 17, wherein the clasping portion includes at least one window.

19. The dental tray of claim 17, wherein at least one distal band is disposed between the two opposing lateral bands and extending downwardly from the top portion, and wherein the receiving cavity of the clasping portion is enclosed by opposing distal bands, the opposing lateral bands, and the top portion.

20. The dental tray of claim 17, wherein the at least one rest is one of an occlusal rest and an incisal rest and the at least one oral structure comprises at least one tooth and wherein the one of the occlusal rest and the incisal rest is shaped to fit the contours of a corresponding surface of the at least one tooth when the clasping portion successfully engages the received at least one oral structure.

21. The dental tray of claim 17, wherein the dental tray is configured to be one of a surgical guide, imaging appliance and a bite splint.

\* \* \* \* \*